United States Patent [19]

Cortes

[11] Patent Number: 5,149,825
[45] Date of Patent: Sep. 22, 1992

[54] 2-AZABICYCLO(2.2.1)HEPT-5-ENE-2-ACETIC ACID, DERIVATIVES THEREOF AND RELATED COMPOUNDS, PROCESS FOR THE PREPARATION OF SAID COMPOUNDS AND THE USE OF SAID COMPOUNDS FOR THE MANUFACTURE OF N-PHOSPHONOMETHYLGLYCINE

[75] Inventor: David A. Cortes, Fairless Hills, Pa.

[73] Assignee: American Cyanamid Company, Stamford, Conn.

[21] Appl. No.: 399,571

[22] Filed: Aug. 31, 1989

Related U.S. Application Data

[63] Continuation-in-part of Ser. No. 276,186, Nov. 23, 1988, Pat. No. 4,946,993.

[51] Int. Cl.$^5$ ............................................. C07D 209/00
[52] U.S. Cl. ...................................... 548/515; 546/112
[58] Field of Search ......................... 548/515; 546/112

[56] References Cited

U.S. PATENT DOCUMENTS 4,053,505 10/1977 Dutra ..................................... 562/18
4,415,503 11/1983 Robbins ................................. 562/18

OTHER PUBLICATIONS

Grieco et al., J. Org. Chem., 52(26):5746:5749 (1987).
U.S. Pharmacopeia pp. 15, 16 (1970).
Ishizumi, K. et al. "Imide drivatives . . . " CA 106:33119f (1987).
Larsen et al. "Aza Diols–Alder Reaction . . . " J. Am. Chem. Soc. 107 1768–1769 (1985).
Grieco et al., "Retro Azo Diels–Alder Reaction . . . ", J. Am. Chem. Soc. 109: 5859–5861, Sep. (1987).
Waldmann et al "Asymmetric hetero-Diols-Alder . . . " CA 110 154114s Apr. (1989).
Fieser and Fieser "Organic Synthesis, Reagents for " John Wiley and Sons Inc. 1 pp. 272, 426 (1967).
Chem. Abst. vol. 110, at 641cs(left col., Lines 25, 26) Chem Substance Index, 1989.

*Primary Examiner*—C. Warren Ivy
*Assistant Examiner*—Celia Chang
*Attorney, Agent, or Firm*—Peggy A. Climenson

[57] ABSTRACT

The present invention describes a novel compound, 2-azabicyclo[2.2.1]hept-5-ene-2-acetic acid, its preparation and the preparation of related compounds, and the use of said compounds as intermediates for the preparation of N-phosphonomethylglycine.

5 Claims, No Drawings

2-AZABICYCLO(2.2.1)HEPT-5-ENE-2-ACETIC ACID, DERIVATIVES THEREOF AND RELATED COMPOUNDS, PROCESS FOR THE PREPARATION OF SAID COMPOUNDS AND THE USE OF SAID COMPOUNDS FOR THE MANUFACTURE OF N-PHOSPHONOMETHYLGLYCINE

This application is a continuation-in-part of application Ser. No. 276,186, filed on Nov. 23, 1988, now U.S. Pat. No. 4,946,993, issued Aug. 7, 1990.

BACKGROUND OF THE INVENTION

The invention herein described relates to a new compound, 2-azabicyclo[2.2.1]hept-2-ene-2-acetic acid, derivatives thereof, the preparation of said new compounds and their use as an intermediate in the process or the manufacture of N-phosphonomethylglycine, a known herbicide and plant growth regulator.

Methyl-2-azabicyclo[2.2.1]hept-5-ene-2-acetate (azanorbornene methyl ester) is described in the literature by Paul A. Grieco in J. Am. Chem. Soc., 1987, 109, pp 5859–5861 and J. Org. Chem. 1987, 52, pp 5746–5749. However, 2-azabioyclo[2.2.1]hept-5-ene-2-acetic acid, the compound and its formation by an Aza Diels-Alder reaction in glacial acetic acid has not been reported in the literature.

N-Phosphonomethylglycine, the compound and its use as an important herbicidal gent is described in U.S. Pat. No. 3,799,758. N-phosphonomethylglycine and derivatives thereof are effective herbicides at low rates of application when applied postemergence and are biodegradable into harmless residues within a relatively short period of time after their application.

A number of processes for the preparation of N-phosphonomethylglycine have been described in a series of patents such as U.S. Pat. Nos. 4,053,505, 4,237,065, 4,415,503, and 4,428,888 among others. Many of these processes use glycinate esters or phosphinate esters, or both, necessitating additional materials and additional reaction steps for their formation.

There is an ongoing search in the art for better methods of preparation of this agronomically important compound. Surprisingly, it has been discovered that 2-azabicyclo[2.2.1]hept-5-ene-2-acetic acid (N-carboxymethylazanorbornene), derivatives thereof and related compounds can be used as key intermediates in a new and useful process to prepare N-phosphonomethylglycine. It is an object of the present invention to describe a novel compound, derivatives of said compound and their preparation and to provide a new and useful method to prepare N-phosphonomethylglycine. These novel intermediates allow the preparation of N-phosphonomethylglycine from glycine and a phosphorous acid equivalent without the use of esters.

SUMMARY OF THE INVENTION

It has now been found that N-substituted azanorbornenes of formula I, wherein Y is COOR, CON($R_1$)$_2$ or CN and R and $R_1$ are each independently hydrogen or $C_1$–$C_4$ alkyl, are useful intermediates for the production of N-phosphonomethylglycine.

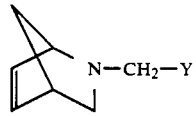

Compounds of formula I as hereinabove described may be formed by reacting aminomethyl compounds of formula II, or their protonated salts, wherein Y is as described above for formula I, with from about 0.90 to 10.0 molar equivalents of formaldehyde and from about 1.0 to 10.0 equivalents of cyclopentadiene in the presence of a solvent, as shown in Flow Diagram I.

FLOW DIAGRAM I

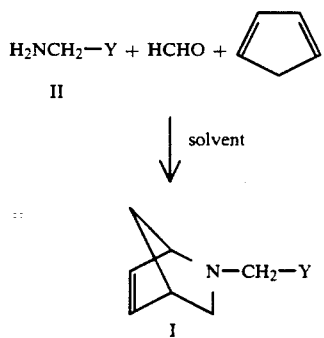

When Y is CON($R_1$)$_2$, COOR or CN, the presence of an acid is required. When Y is COOH, no additional acid is needed.

Dienes other than cyclopentadiene such as substituted cyclopentadienes, may also be employed in the reaction sequence illustrated in Flow Diagram I to give the corresponding azanorbornenes.

The N-substituted azabicycloalkene intermediates so obtained, such as the N-substituted azanorbornene intermediates of formula I, preferably wherein Y is COOH, may be reacted with a phosphorous acid equivalent such as dialkylphosphite or a phosphorous trihalide, preferably phosphorous trichloride, in the presence of a solvent, preferably a $C_1$–$C_4$ alkyl carboxylic acid, preferably acetic acid, optionally followed by hydrolysis in the presence of aqueous acid or base, preferably acid, to produce N-phosphonomethylglycine as ilustrated in Flow Diagram II, wherein Y is as described hereinabove, $R_2$ is H or $C_1$–$C_4$ alkyl, and X is Cl or Br.

FLOW DIAGRAM II

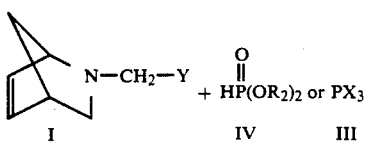

-continued
FLOW DIAGRAM II

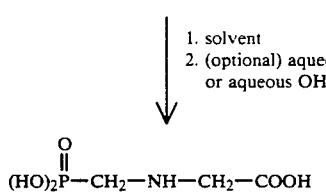

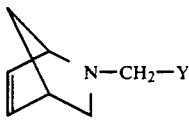

DESCRIPTION OF THE INVENTION

The invention relates to a novel compound, 2-azabicyclo[2.2.1]hept-5-ene-2-acetic acid, derivatives thereof and related compounds, the preparation of said compounds and a novel method to prepare N-phosphonomethylglycine via the N-substituted azabicycloalkene intermediates such as the N-substituted azanobornene intermediate of formula I

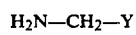 I wherein Y is COOR, $CON(R_1)_2$, OR CN; and R and $R_1$ are each independently hydrogen or $C_1$–$C_4$ alkyl.

Compounds of formula I may be prepared by reacting aminomethyl compounds of formula II or the protonated salts thereof, wherein Y is as described for formula I, with from about 0.9 to 10 0 molar equivalents of formaldehyde and from about 1 to 10 molar equivalents of cyclopentadiene in a solvent. The reaction is acid catalyzed; therefore, in the absence of an acid solvent, a protonated salt of the aminomethyl compound of formula II is used. The formaldehyde used may be any of the common forms available, such as: 37% aqueous formaldehyde (formalin); a solution of 55% formaldehyde, 35% methanol and 10% water (methyl formcel); or solid paraformaldehyde. Solvents which may be used should allow at least some of the protonated form of II to be in solution. Typical solvents are water or mixtures of water and a miscible organic solvent. Surprisingly, a $C_1$–$C_4$ alkyl carboxylic acid, and preferably acetic acid, may also be used.

The reaction proceeds at a convenient rate at 25° C.–30° C. except when solid paraformaldehyde is used, in which case the formation of I depends on the rate of depolymerization of pereformaldehyde. Said rate of depolymerization is increased by decreasing the particle size of the paraformaldehyde used or heating the paraformaldehyde with acid before the addition of an aminomethyl compound of formula II such as glycine.

Other dienes that may be used in the above-described process re substituted cyclopentadienes. The substituents on cyclopentadiene may be $C_1$–$C_4$ alkyl, aryl and $NO_2$.

Using the above-said dienes, N-substituted azabicyclohexene compounds of formula V

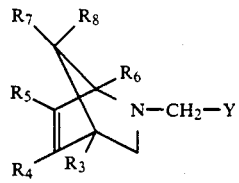 V wherein $R_3$, $R_4$, $R_5$, $R_6$, $R_7$ and $R_8$ are each independently hydrogen, $C_1$–$C_4$ alkyl, $C_6H_5$ or $NO_2$; Y is COOR, $CON(R_1)_2$ or CN wherein R, $R_1$ are each independently hydrogen or $C_1$–$C_4$ alkyl may be prepared by reacting an aminomethyl compound of formula II $$H_2N-CH_2-Y$$  II wherein Y is as described hereinabove for formula v with 0.9 to 10.0 molar equivalents of formaldehyde and 1.0 to 10.0 molar equivalents of a diene of formula VI

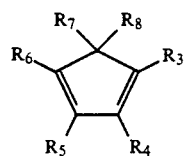 VI wherein $R_3$, $R_4$, $R_5$, $R_6$, $R_7$ and $R_8$ are as described hereinabove for formula V, in the presence of a solvent, preferably glacial acetic acid, at a temperature range of from 15° C. to 200° C. for a period of 1 to 24 hours.

It is an important feature of the process of the invention that the presence of water in the N-substituted azabicycloalkene intermediate be minimized. Since water reacts with compounds of formula III, the amount of water present in the reaction mixtures should be less than three equivalents. The presence of water in the reaction of an N-substituted azabicycloalkene with compounds of formula IV results in the formation of undesirable side products. When Y is CN, $CON(R_1)_2$ or COOR and $R_1$ or R is $C_1$–$C_4$ alkyl in formula I, the N-carboalkoxymethylazabicycloalkene can be extracted into organic solvents and water can be conveniently removed. However, when Y is COOH the resulting N-carboxymethylazabicycloalkene is highly water soluble and the removal of water therefrom requires distillation. Reduced pressure distillation steps may be required when the azabicycloalkene compound is N-carboxymethylazanorbornene, since said compound decomposes at a significant rate above 40° C. Utilization of acetic acid as the preferred solvent when Y is COOH, and either paraformaldehyde or methyl formcel as the preferred form of formaldehyde, minimizes the amount of water present in the N-carboxymethylazabicycloalkene intermediate. If methyl formcel is used, as much methanol as possible should be removed under reduced pressure before the next step as the presence of methanol retards the rate of reaction. Since water is a product of the reaction shown in Flow Diagram I, approximately 1 mole of water per mole of N-substituted azabicyclohexene is typically present in the product acetic acid solution.

2-Azabicyclo[2.2.1]-hept-5-ene-2-acetic acid is a zwitterionic compound at neutral pH. Said compound may be obtained as a solid by the removal of water, dissolution in ethanol and the removal of ethanol to give a solid residue which after washing with acetone, gives a white hygroscopic solid which decomposes gradually from 90° C.–135° C. Neutral and acidic solutions of 2-azabicyclo[2.2.1]-hept-5-ene-2-acetic acid are unstable due to the propensity of the compound to undergo the retro Diels-Alder reaction. Said solutions should be stored at temperatures below 10° C. The decomposition rate is such that about 25% decomposition occurs over one month at 10° C.

Other N-substituted azabicycloalkene compounds which may be prepared by the method of the invention as described hereinabove are:
2-azabicyclo-[2.2.1]hept-5-ene-acetonitrile;
2-azabicyclo[2.2.1]hept-5-ene-2-acetamide;
N,N-dimethyl-2-azabicyclo[2.2.1]hept-5-ene-2-acetamide;
N-methyl-2-azabicyclo[2.2.1]hept-5-ene-2-acetamide;
4,5,7-trimethyl-2-azabicyclo[2.2.1]hept-5-ene-2-acetic acid;
7-methyl-2-azabicyclo[2.2.1]hept-5-ene-2-acetic acid;
6-methyl-2-azabicyclo[2.2.1]hept-5-ene-2-acetic acid;
5-methyl-2-azabicyclo[2.2.1]hept-5-ene-2-acetic acid;
4-methyl-2-azabicyclo[2.2.1]hept-5-ene-2-acetic acid;
3-methyl-2-azabicyclo[2.2.1]hept-5-ene-2-acetic acid;
1-methyl-2-azabicyclo[2.2.1]hept-5-ene-2-acetic acid; and
4,5,6,7-tetramethyl-2-azabicyclo[2.2.1]hept-5-ene-2-acetic acid.

N-substituted azabicycloalkene intermediates, such as the N-substituted azanorbornene intermediates of formula I, are reacted with from about 1.0 to 5.0 molar equivalents of a phosphorous compound of formula III or IV, as shown below,

wherein X is halogen and $R_2$ is H, $C_1$–$C_4$ alkyl, in the presence of a solvent such as an aromatic hydrocarbon, a halogenated aromatic hydrocarbon, a halogenated hydrocarbon, a lower alkyl alcohol or acetonitrile, or a $C_1$–$C_4$ carboxylic acid, preferably acetic acid, at a temperature such that the reaction proceeds at a convenient rate. The rate depends on the temperature at which the protonated N-substituted azabicycloalkene intermediate undergoes the retro Diels-Alder reaction in the particular solvent that is used. If compounds of formula III are used in the presence of a non-hydroxylated solvent, then a stoichiometric amount of an hydroxylated compound is required. A key aspect of this reaction is that the nitrogen in the intermediates of formula V be partially tetracoordinated. Typical temperatures are about 20° C.–120° C., preferably about 35° C.–80° C.; said temperatures produce a reaction time of 2 to 24 hours. If a phosphorous compound of formula IV is used, the product of the reaction is an ester which can be hydrolyzed using standard procedures such as removal of the solvent in vacuo, followed by treatment of the residue with either aqueous mineral acid or aqueous alkali base and heating to a temperature range of from about 30° C.–100° C. until hydrolysis is complete to give N-phosphonomethylglycine. If a phosphorous compound of formula III is used in the presence of acetic acid, the major product of the reaction is an N-acetylated compound of formula VII which is hydrolyzed by combining the reaction mixture with about 1 to 5 parts by volume of water and heating at reflux temperatures. Hydrolysis is complete in about 3–6 hours at 100° C.

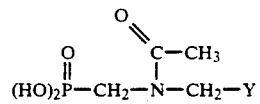

The addition of $PX_3$ is carried out with cooling to temperatures below 30° C. Using phosphorous compounds of either formula III or IV, isolation of the product N-phosphonomethylglycine from the hydrolysis reaction is achieved by the removal of side products by filtration, concentration of the filtrate, adjustment of the pH to 1.3–1.5 to precipitate the desired product, and filtration of the N-phosphonomethylglycine product.

A preferred embodiment of this invention is an integrated, single pot process wherein the N-substituted azabicycloalkene intermediate is an azanorbornene compound of formula I, preferably wherein Y is COOH, and is generated in situ by reacting glycine with from about 1.0 to 1.5 molar equivalents of formaldehyde and from about 1.0 to 2.5 molar equivalents of cyclopentadiene in the presence of glacial acetic acid at a temperature range of from about 20°–40° C., preferably 25°–35° C., for from about 1 to 24 hours; then treating this reaction mixture with from about 1.0 to 3.0 molar equivalents of a phosphorous trihalide, preferably 1.0 to 1.5 molar equivalents of phosphorous trichloride, and heating at a temperature range of from about 35°–60° C. for 5 to 16 hours; followed by combining the cooled reaction mixture with from about 1.0 to 5.0 parts by volume of water, filtering, heating at reflux to hydrolyze the N-acetyl compound of formula VII, distilling the filtrate to reduce the volume to that volume prior to combination of the reaction mixture with water, followed by cooling, filtering again and treating the filtrate with sufficient aqueous base to adjust the pH to about 1.3 to 1.5 and isolating the product N-phosphonomethylglycine by filtration. Alternatively, hydrolysis and isolation of the product N-phosphonomethylglycine may be achieved by the addition of 5 to 30 molar equivalents of water (0.1 to 1.0 parts by volume) to the cooled reaction mixture following the period of heating with phosphorous trichloride. The reaction mixture is then heated at reflux temperatures for 2 to 24 hours, cooled and filtered. The solid filter cake is recrystallized from water to give the product N-phosphonomethylglycine.

In order to facilitate a further understanding of the invention, the following examples are presented primarily for the purpose of illustrating more specific details thereof. The invention is not to be limited thereby except as defined in the claims. Unless otherwise noted, all parts are by weight. The term NMR designates nuclear magnetic resonance and, the term HPLC designates high pressure liquid chromatography.

EXAMPLE 1

Preparation of 2-azabicyclo[2.2.1]hept-5-ene acetic acid in acetic acid

A stirred mixture of glycine (7.5 g, 0.10 mole) in 35 mL of acetic acid is treated with formalin, 37% (11.3 g, 0.14 mol formaldehyde) followed by cyclopentadiene (13.2 g, 0.20 mole). After stirring for 3 hours at 25° C., a clear solution is obtained. HPLC analysis indicates the solution is 25% 2-azabicyclo[2.2.1]hept-5-ene acetic acid (N-carboxymethylazanorbornene) (quantitative yield).

EXAMPLE 2

Preparation of 2-azabicyclo[2.2.1]hept-5-ene acetic acid in water

A stirred mixture of glycine (37.5 g, 0.50 mole), 165 mL water and formalin, 37% (57 g, 0.70 mole formaldehyde) is treated with cyclopentadiene (66.0 g, 1.0 mole) at 25° C.–34° C. The reaction mixture is stirred rapidly for 15 hours, then separated to give 284.4 g of a 25% aqueous solution of the titled compound by HPLC analysis (93% yield).

The water is removed in vacuo from a portion of this aqueous solution, and the residue dissolved in a small amount of ethanol followed by removal of the ethanol in vacuo to give a solid residue. This residue is washed with acetone to give the titled product as a hygroscopic, white solid which decomposes gradually over a temperature range of 90° C.–125° C. The product is identified by proton and carbon NMR spectral analyses.

EXAMPLE 3

Preparation of N-pohosphonomethylglycine via an N-substituted azanorbornene intermediate and phosphorous trichloride in acetic acid A stirred mixture of N-carboxymethylazanorbornene (4.7 g, 0.030 mole) in 40 mL of acetic acid is treated with phosphorous trichloride (8.2 g, 0.060 mole) over a 10 minute period at 20° C.–25° C. The reaction mixture is heated at 35° C.–40° C. for 6 hours, cooled to 25° C. over a 16 hour period, then combined with 100 mL water. After filtration, the filtrate is heated at reflux for 6 hours then concentrated to a final volume of 40 mL by distillation. After cooling to 20° C. and filtering, the filtrate is treated with 50% NaOH to pH 1.5. This mixture is further concentrated and cooled to yield a solid precipitate. This solid is shown to be the titled product by HPLC analysis in 46% yield and 87% purity.

EXAMPLE 4

Preparation of N-phosphonomethylglycine via an N-substituted azanorbornene intermediate and phosphorous trichloride in propionic acid A stirred mixture of N-carboxymethylazanorbornene (4.6 g, 0.030 mole) in 40 mL of propionic acid is treated with phosphorous trichloride (8.2 g, 0.060 mole) over a 10 minute period at 20° C.–25° C. The reaction mixture is heated at 45° C.–50° C. for 4 hours, followed by heating at 74° C.–80° C. for 1 hour. After evaporation of the majority of the propionic acid in vacuo, the residue is dispersed in 75 mL of water and heated at reflux for 16 hours. Cooling to 25° C. and filtration of the reaction mixture gives a filtrate which contains the titled product in 55–60% yield by HPLC analysis.

EXAMPLE 5

Preparation of N-phosphonomethylglycine via 2-azabicyclo[2.2.1]-hept-5-ene acetic acid in a single integrated process A stirred mixture of glycine (15.0 g, 0.20 mole) and methyl formcel (55% formaldehyde, 10% water and 35% methanol) (12.2 g, 0.22 mole formaldehyde) in 60 mL glacial acetic acid at 20° C. is treated with cyclopentadiene (16.5 g, 0.25 mole). The temperature is kept at 25° C.–30° C. with ice-bath cooling to control the exotherm. The reaction is stirred at 25° C.–30° C. for 3 hours, followed by 3 hours at 25° C. under 25 inches of mercury vacuum. (HPLC assay indicates approximately 91% yield of 2-azabicyclo[2.2.1]hept-5-ene-2-acetic acid.)

The stirred reaction is treated with phosphorous trichloride (34.3 g, 0.25 mole) at 25° C., heated at 40° C.–45° C. for 4 hours, cooled to 20° C.–25° C. and added to 350 mL of water with stirring. The reaction mixture is filtered and the filter cake is washed with 50 mL of water. The combined filtrates are concentrated by distillation at 100° C.–105° C. until approximately 350 mL of distillate is collected. The reaction is cooled to 20° C.–25° C., filtered and the filtrate is treated with 50% NaOH solution to pH 1.4. The resultant precipitate is filtered to give N-phosphonomethylglycine as a grey solid, wt=28.7 g, HPLC assay indicates 63% purity.

EXAMPLE 6

Preparation of N-phosphonomethylglycine via an N-carboxymethylazanorbornene intermediate and dimethylphosphite A stirred mixture of a 25% aqueous solution of N-carboxymethylazanorbornene (5.9 g, 0.010 mole) and 15 mL of acetic acid is treated with dimethyl phosphite (1.65 g, 0.015 mole) and heated at 80° C. for 3 hours. The reaction mixture is cooled to 25° C. and concentrated in vacuo. The residue is dispersed in 10 mL of concentrated HCl and 4 mL water and heated at reflux for 3 hours. After filtration, the filtrate is shown to contain the titled product by HPLC and NMR analyses.

EXAMPLE 7

Preparation of ethyl 2-azabicyclo[2.2.1]hept-5-ene-2-acetate (N-carboethoxymethylazanorbornene)

To a stirred solution of glycine ethyl ester hydrochloride salt (27.9 g, 0.20 mole) in 80 mL water is added formalin, 37% (22.7 g, 0.28 mole formaldehyde) followed by cyclopentadine (26 g, 0.40 mole). The two phase reaction mixture is stirred rapidly for 4 hours, then separated. The aqueous phase is extracted with methylene chloride, then treated with 50% sodium hydroxide, with cooling to maintain a temperature of 20° C.–25° C., to pH 12. The aqueous mixture is extracted with methylene chloride and this organic phase is concentrated in vacuo to give ethyl 2-azabicyclo[2.2.1]hept-5-ene-2-acetate as an oil, 30.0 g, 83% yield. The product is identified by proton and carbon NMR analyses.

EXAMPLE 8

Preparation of N-phosphonomethylglycine via an N-carboethoxymethylazanorbornene intermediate and phosphorous trichloride in acetic acid A stirred mixture of N-carboethoxymethylazanorbornene (9.05 g, 0.050 mole) in 25 mL of acetic acid is treated with phosphorous trichloride, (10.3 g, 0.075 mole) at 15° C.–20° C. and then heated at 37° C.–43° C. for 6 hours. After cooling to 25° C., the reaction mixture is added dropwise to 100 mL of water to give a slurry. The solid is removed by filtration, and the filtrate is concentrated to about 50 mL by distillation at 100° C. during which time the N-acetyl compound is hydrolyzed. The mixture is cooled to 25° C. and filtered. The pH of the filtrate is adjusted to 1.4 with 50% NaOH and is cooled to 10° C. The precipitate that forms is filtered to give 6.0 g of N-phosphonomethylglycine, 66% yield, 93% purity by HPLC analysis.

EXAMPLE 9

Preparation of N-phosphonomethylglycine via an N-carboethoxymethylazanorbornene intermediate and dimethylphosphite A stirred solution of N-carboethoxymethylazanorbornene (1.8 g, 0.010 mole) in 10 mL of acetonitrile is treated with dimethylphosphite (2.2 g, 0.020 mole) and heated at reflux temperatures for 2 hours. The reaction is cooled to room temperature and concentrated in vacuo. The residue is dispersed in 10 mL of 3N HCl and heated at reflux temperatures for approximately 8 hours. HPLC analysis indicates a 50% yield of N-phosphonomethylglycine.

EXAMPLE 10

Preparation of N-phosphonomethylglycine via an N-carboethoxymethylazanorbornene intermediate and 1.0 equivalent of diethylphosphite A stirred solution of N-carboethoxymethylazanorbornene (1.8 g, 0.010 mole) in 10 mL of acetonitrile is treated with diethylphosphite (1.4 g, 0.010 mole) and heated at reflux for 2 hours. The reaction is cooled to room temperature and concentrated in vacuo. The residue is dispersed in 15 mL of 3.4N NaOH solution and heated at reflux temperatures for 3 hours, then cooled to 30° C., treated with concentrated HCl to pH 1.5, and filtered. Analysis of the filtrate by HPLC indicates a 40% yield of N-phosphonomethylglycine.

EXAMPLE 11

Preparation of N-phosphonomethylglycine via N-carboethoxymethylazanorbornene and 2.0 equivalents of diethylphosphite A stirred solution of N-carboethoxymethylazanorbornene (1.8 g, 0.010 mole) in 10 mL of ethanol is treated with diethyl phosphite (2.7 g, 0.20 mole) and heated at reflux temperatures for 2 hours. The reaction mixture is cooled to 25° C. and concentrated in vacuo. The residue is dispersed in concentrated HCl and heated to reflux temperatures until hydrolysis is complete by HPLC analysis. The reaction mixture is cooled to 25° C. and treated with 50% NaOH solution to pH 1.5 and filtered. The filtrate is concentrated in vacuo and the residue is slurried in water and filtered to give the titled product in 40% yield as a solid, identified by HPLC and NMR analyses.

EXAMPLE 12

Preparation of methyl 2-azabicyclo[2.2.1]hept-5-ene-5-methyl-2-acetate

A solution of methyl glycinate hydrochloride (25.1 g, 0.20 mole) in water is treated with 37% formalin (27.7 g, 0.28 mol formaldehyde), cooled to 10° C., treated with methylcyclopentadiene (32.0 g, 0.40 mol) in a single portion and stirred for 2.5 hours. The reaction mixture is separated and the aqueous phase is extracted with methylene chloride and basified to pH >12 with 50% NaOH at <25° C. The basic aqueous phase is extracted with methylene chloride. The methylene chloride extracts are combined and concentrated in vacuo to give the title compound (N-carbomethoxymethyl- 5-methylazanorbornene) as an oil, 26.2 g, which can be distilled at 80°–90° C./1.0 torr. The compound is identified by NMR and mass spectral analyses.

EXAMPLE 13

Preparation of N-phosphonomethylglycine via N-carbomethoxymethyl-5-methylazanorbornene A solution of N-carbomethoxymethyl-5-methylazanorbornene (0.91 g, 5.0 mmol) in acetic acid is treated portionwise with phosphorous trichloride (1.03 g, 7.5 mmol), heated at 45°–50° C. for 5 hours, treated with water and heated at reflux temperature for 5 hours. The reaction mixture is cooled to room temperature, filtered, and the filtrate is concentrated in vacuo to give the title product in 61% yield by HPLC analysis.

EXAMPLE 14

Preparation of 2-azabicyclo[2.2.1]hept-5-ene-2-acetonitrile

A solution of aminoacetonitrile hydrochloride (18.5 g, 0.20 mol) in water at 5° C. is treated with 37% formalin (23.0 g, 0.28 mol formaldehyde) followed by cyclopentadiene (26.0 g, 0.4 mol), stirred at 5°–10° C. for 30 minutes and diluted with methylene chloride. The phases are separated, the aqueous phase is extracted with methylene chloride and basified to pH >12 with 10% NaOH. The aqueous basic phase is extracted with methylene chloride. The methylene chloride extract of the basic aqueous phase is concentrated in vacuo to give the title product (N-cyanomethylazanorbornene), 22.7 g, which can be distilled at 68°–70° C./0.55 torr. The compound is identified by NMR and mass spectral analyses.

EXAMPLE 15

Preparation of N-phosphonomethylglycine via N-cyanomethylazanorbornene

A solution of N-cyanomethylazanorbornene (9.80 g, 0.073 mol) in acetic acid is treated with phosphorous trichloride (11.6 g, 0.085 mol) over a 5 minute period at 25°–37° C., heated at 50° C. for 3 hours, treated with water and heated at reflux temperature until hydrolysis is complete by HPLC assay. The reaction mixture is cooled to room temperature and filtered. HPLC analysis of the filtrate and filter cake indicates a 24% yield of the title product.

EXAMPLE 16

Preparation of 2-azabicyclo[2.2.1]hept-5-ene-2-acetamide

A solution of glycinamide hydrochloride 22.1 g, 0.20 mol) in water is treated with 37% formalin (23.0 g, 0.28 mol formaldehyde) cooled to 10° C., treated with cyclopentadiene (26.4 g, 0.40 mol), stirred for 3 hours at 5°–10° C., and diluted with methylene chloride. The phases are separated. The aqueous phase is extracted with methylene chloride and basified with 10% NaOH to pH 12 with cooling. The aqueous basic phase is extracted with methylene chloride. The methylene chloride extracts of the basic aqueous phase are combined and concentrated in vacuo to give the title product (N-carboxamidomethylazanorbornene) as a solid, 17.6 g, mp 74°–96° C. which can be purified by sublimation at 120° C./0.55 torr. The compound is identified by NMR and mass spectral analyses.

EXAMPLE 17

Preparation of N-phosphonomethylglycine via N-carboxamidomethylazanorbornene

A solution of N-carboxamidomethylazanorbornene (5.0 g, 0.033 mol) in acetic acid is treated with phosphorous trichloride (5.3 g, 0.038 mol) over a 2 minute period, heated at 50° C. for 3.5 hours, treated with water and heated at reflux temperature until hydrolysis is complete by HPLC assay. The reaction mixture is cooled and filtered. HPLC analysis of the filtrate and filter cake indicates a 42% yield of the title product.

EXAMPLE 18

Preparation of N-phosphonomethylglycine via an N-carbomethoxymethylazanorbornene intermediate in the presence of a variety of non-oxygenated solvents A stirred solution of N-carbomethoxymethylazanorbornene (15.9 g, 0.095 mol) in a non-oxygenated solvent is treated with water (4.3 g, 0.239 mol), followed by the addition of phosphorous trichloride over a 10 minute period. The reaction mixture is heated at 50° C. for 4 hours, cooled, treated with additional water and heated at reflux temperature until HPLC assay indicates hydrolysis is complete. The reaction mixture is cooled and filtered. The filtrate is separated and the aqueous phase is analyzed by HPLC for the presence of the title product.

For each experiment, a portion of the final aqueous phase is concentrated in vacuo and the title product is identified by $^1$H and $^{13}$C NMR spectral analyses.

| Experiment | Solvent | PCl$_3$ | Yield |
|---|---|---|---|
| 1 | Ethylene dichloride | 0.17 mol | good |
| 2 | Acetonitrile | 0.17 mol | good |
| 3 | Toluene | 0.16 mol | 65% |
| 4 | Toluene | 0.11 mol | 67% |

I claim:

1. A compound having the structure

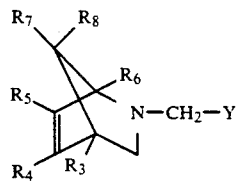

V wherein $R_3$, $R_4$, $R_5$, $R_6$, $R_7$ and $R_8$ are each independently hydrogen, $C_1$-$C_4$ alkyl, $C_6H_5$ or $NO_2$; and Y is $CON(R_1)_2$ or CN wherein $R_1$ is hydrogen or $C_1$-$C_4$ alkyl.

2. The compound according to claim 1, 2-azabicyclo[2.2.1]hept-5-ene-2-acetonitrile.

3. The compound according to claim 1, 2-azabicyclo[2.2.1]hept-5-ene-2-acetamide.

4. A method for the preparation of an azabicycloalkene compound having the structure

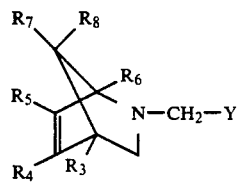

V wherein $R_3$, $R_4$, $R_5$, $R_6$, $R_7$ and $R_8$ are each independently hydrogen, $C_1$-$C_4$ alkyl, $C_6H_5$ or $NO_2$; and Y is COOH; which consists essentially of reacting $H_2N$—$CH_2$—COOH with formaldehyde and a cyclopentadiene compound of Formula VI

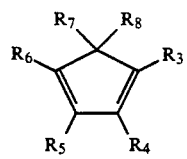

VI wherein $R_3$, $R_4$, $R_5$, $R_6$, $R_7$ and $R_8$ are as described in Formula V, in the presence of a non-aqueous $C_1$-$C_4$ alkyl carboxylic acid.

5. The method according to claim 4, wherein $R_3$, $R_4$, $R_5$, $R_6$, $R_7$ and $R_8$ of formula VI are hydrogen and the acid is glacial acetic acid.

* * * * *